United States Patent [19]

Reinehr

[11] 4,289,905
[45] Sep. 15, 1981

[54] 2-AZA-1,3-DIENES

[75] Inventor: Dieter Reinehr, Kandern, Fed. Rep. of Germany

[73] Assignee: Ciba-Geigy Corporation, Ardsley, N.Y.

[21] Appl. No.: 923,438

[22] Filed: Jul. 10, 1978

[30] Foreign Application Priority Data

Jul. 19, 1977 [CH] Switzerland ............... 8916/77

[51] Int. Cl.³ .................................... C07C 119/00
[52] U.S. Cl. ................................... 564/248; 564/279
[58] Field of Search ............... 260/566 R; 564/248, 564/279

[56] References Cited

U.S. PATENT DOCUMENTS 2,319,848  5/1943  Clark et al. ............... 260/566 R
2,535,922  12/1950 Haury et al. ............... 260/566 R

FOREIGN PATENT DOCUMENTS 1049853  2/1959  Fed. Rep. of Germany ... 260/566 R
101606   6/1962  Netherlands ............... 260/566 R
1380304  1/1975  United Kingdom .

OTHER PUBLICATIONS

Worley, S. D. et al., *Tetrahedron*, vol. 34 (1978), pp. 833-839.
Hasek, Robert H. et al., *J. Organic Chemistry*, vol. 26 (1961), pp. 1822-1825.
Houben-Weyl, "Methoden der organischen Chemie", vol. 4/2 (1955), pp. 407-410 and vol. 11/1 (circa 1957), p. 297.
Beilstein, "Organische Chemie", vol. 4, p. 203 (1922); vol. E II 4, p. 661 (1942); and vol. E III, p. 442 (1962).
Malhotra et al., *J. Am. Chem. Soc.*, vol. 89 (1967), pp. 2974-2975.
Kazanskii, B. A. et al., *Zhurnal Organicheskoi Khimii*, vol. 6, (1970), pp. 2197-2199, translation by Plenum Publ. Co.
Dol'skaya, Yu. S. et al., *Izw. Akad. Nauk. SSSR, Ser. Khim*, vol. 9 (1975), pp. 2038-2045, translation by Plenum Publ. Co.

*Primary Examiner*—Natalie Trousof
*Assistant Examiner*—L. Hendriksen
*Attorney, Agent, or Firm*—Michael W. Glynn

[57] ABSTRACT

There are described compounds of the formula

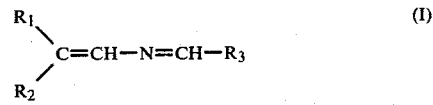

wherein $R_1$ and $R_2$ independently of one another represent alkyl having 1–8 C atoms, or together with the bond C atom they represent a cycloaliphatic ring having 4–8 C atoms, and $R_3$ represents ethyl; or wherein $R_1$ represents alkyl having 1–8 C atoms, $R_2$ represents hydrogen, or alkyl having 1–8 C atoms, and $R_3$ represents tertiary alkyl having 4–8 C atoms.

The compounds of the formula I can be produced in a simple manner, in good to very good yields, by isomerisation of suitably substituted allylamines in an inert organic solvent and in the presence of a catalyst. The compounds of the formula I constitute valuable intermediates for producing active substances for combating plant pests.

7 Claims, No Drawings

2-AZA-1,3-DIENES

The present invention relates to new 2-aza-1,3-dienes, and to a process for producing them.

It is known from the literature [B. A. Kazanskii et al., Zhurnal Organicheskoi Khimii, Vol. 6, No. 11, pp. 2197-99, Nov. 1970] that certain allylalkylideneimines in the presence of $K_2O/Al_2O_3$ catalysts can be isomerised at temperatures between 135° and 250° C. to give conjugated 2-aza-1,3-dienes. The yield of 2-aza-1,3-dienes with this process is however very low (between about 6.5 and 22% of theory). According to Izw.Akad. Nauk.SSSR, Ser.Khim., No. 9, 2038-2045 (1975), allylalkylideneimines, and particularly allylbenzylideneimines, can be isomerised, with in part somewhat better yields, in the presence of aluminium/potassium catalysts or aluminium/chromium/potassium catalysts at temperatures between 250° and 350° C. to give 2-aza-1,3-dienes. On account of these high reaction temperatures, these known processes are limited in their application to particularly stable starting products, and furthermore they are uneconomical. It is also known that benzylamine Schiff bases of $\alpha,\beta$-unsaturated ketones can be isomerised in the presence of potassium tert-butylate or p-toluenesulphonic acid, and optionally in the presence of an inert organic solvent, to yield corresponding 2-aza-1,3-dienes. These 2-aza-1,3-dienes were not however isolated [J.Am.Chem.Soc., 89, 2794-2795 (1967)].

The object of the present invention was to render available new 2-aza-1,3-dienes in a simple manner.

The new 2-aza-1,3-dienes correspond to the formula I

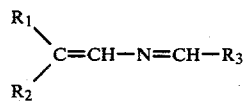

wherein $R_1$ and $R_2$ independently of one another represent alkyl having 1-8 C atoms, or together with the bond C atom they represent a cycloaliphatic ring having 4-8 C atoms, and $R_3$ represents ethyl; or $R_1$ represents alkyl having 1-8 C atoms, $R_2$ represents hydrogen, or alkyl having 1-8 C atoms, and $R_3$ represents tertiary alkyl having 4-8 C atoms.

The new compounds of the formula I can be obtained in a simple and economical manner, under mild reactions conditions and with good to very good yields, by isomerising either a compound of the formula IIa

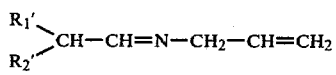

wherein $R_1'$ and $R_2'$ independently of one another represent alkyl having 1-8 C atoms, or together with the bond C atom they represent a cycloaliphatic ring having 4-8 C atoms, or a compound of the formula IIb

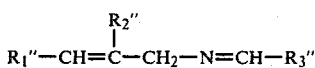

wherein $R_1''$ represents hydrogen, or alkyl having 1-7 C atoms, $R_2''$ represents hydrogen, or alkyl having 1-8 C atoms, and $R_3''$ represents tertiary alkyl having 4-8 C atoms, at a temperature of about 0° to 80° C., preferably about 10° to 50° C., in an inert organic solvent, in the presence of a catalyst of the formula III

wherein

X represents an alkali metal ion or alkaline-earth metal ion,

Y represents alkyl having 1-12 C atoms, and n represents the charge of the alkali metal ion or alkaline-earth metal ion.

With use of starting materials of the formula IIa, there are obtained compounds of the formula I wherein $R_1$ and $R_2$ independently of one another represent alkyl having 1-8 C atoms, or together with the bond C atom they represent a cycloaliphatic ring having 4-8 C atoms, and $R_3$ represents ethyl; whereas with use of starting materials of the formula IIb, there are obtained compounds of the formula I wherein $R_1$ represents alkyl having 1-8 C atoms, $R_2$ represents hydrogen, or alkyl having 1-8 C atoms, and $R_3$ represents tertiary alkyl having 4-8 C atoms.

Alkyl groups represented by $R_1$, $R_2$, $R_1'$, $R_2'$, $R_1''$ and $R_2''$ can be straight-chain or branched-chain. The said groups preferably contain 1-4 or 1-3 C atoms ($R_1'$). Examples which may be mentioned are: the methyl, ethyl, n-propyl, isopropyl, n-butyl, sec-butyl, tert-butyl, n-pentyl, n-hexyl, n-heptyl and n-octyl groups.

As a tertiary alkyl group, $R_3$ or $R_3''$ preferably represents the tert-butyl group.

If $R_1$ and $R_2$ or $R_1'$ and $R_2'$ together with the bond C atom form a cycloaliphatic ring, such rings are in particular unsubstituted cycloalkyl rings. Preferably, the stated substituents form with the bond C atom a cyclopentyl group and especially a cyclohexyl group.

Preferred compounds of the formula I are those wherein $R_1$ and $R_2$ independently of one another represent alkyl having 1-4 C atoms, or together with the bond C atom they represent cyclopentyl and in particular cyclohexyl, and $R_3$ represents ethyl; and also compounds of the formula I wherein $R_1$ represents alkyl having 1-4 C atoms, especially methyl, $R_2$ represents hydrogen, or alkyl having 1-4 C atoms, particularly methyl, and $R_3$ represents tert-butyl.

Particularly preferred compounds of the formula I are those wherein $R_1$ and $R_2$ each represent methyl, and $R_3$ represents ethyl; or wherein $R_1$ represents methyl, $R_2$ represents hydrogen, and $R_3$ represents tert-butyl.

The starting products of the formulae IIa and IIb are known per se, or they can be produced by methods known per se; for example by reaction of aldehydes of the formula

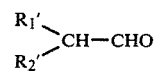

with allylamine; or by reaction of an amine of the formula

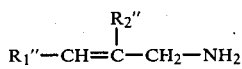

with an aldehyde of the formula

OCH—$R_3''$.

In the formula III, X represents, for example, lithium, potassium, sodium, magnesium, calcium or barium. Preferably, X represents an alkali metal, particularly sodium or potassium. The alkyl groups Y can be straight-chain or branched-chain, and preferably have 1–6 C atoms, and especially 1–4 C atoms. Particularly preferred compounds of the formula III are sodium methylate or potassium methylate, sodium ethylate or potassium ethylate, sodium isopropylate or potassium isopropylate, and particularly sodium tert-butylate or potassium tert-butylate.

The inert organic solvents used in the process according to the invention are advantageously aprotic organic solvents, particularly aliphatic or aromatic hydrocarbons, aliphatic or cyclic ethers, ethylene glycol dialkyl ethers and diethylene glycol dialkyl ethers, dialkyl sulphoxides having 1–4 C atoms in each alkyl moiety, or N,N-dialkylamides of aliphatic monocarboxylic acids having 1–3 C atoms in the acid part, as well as hexamethylphosphoric acid triamide, and alcohols having at least 4 C atoms. Examples of such solvents are: n-pentane, n-hexane, n-heptane, benzene, toluene, xylenes, diethyl ether, di-n-propyl ether, tetrahydrofuran, tetrahydropyrane, dioxane, ethylene glycol dimethyl ether and diethylene glycol dimethyl ether, and ethylene glycol diethyl ether and diethylene glycol diethyl ether, dimethyl sulphoxide, N,N-dimethylformamide, n-butanol, tert-butanol or n-hexanol.

Preferred solvents are n-pentane, benzene, toluene, diethyl ether and tetrahydrofuran.

The catalysts of the formula III are preferably used in an amount of at least 0.1 mol %, relative to the starting product of the formula IIa or IIb. Preferred amounts are about 0.5 to 15 mol %, relative to the compound of the formula IIa or IIb.

Reaction temperatures between about 10° and 50° C. have proved particularly favourable. The isomerisation is performed in many cases at room temperature (20°–25° C.).

The compounds of the formula I can be isolated in a manner known per se, for example by distillation. They are obtained generally in the form of colourless to slightly yellowish liquids. The yields are in general between about 70 and 100% of theory.

The compounds of the formula I are valuable intermediates for producing active substances for combating plant pests, particularly phytopathogenic fungi.

Active substances of this kind can be produced, for example, by reacting a compound of the formula I in the presence of a catalyst obtained by reduction of a nickel compound free from carbon monoxide, in the presence of a chelating olefin and optionally in the presence of an electron donor, at temperatures of between about −40° C. and +150° C., with a compound of the formula IV

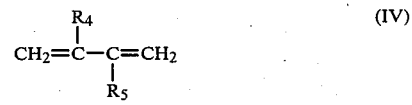

to give a compound of the formula V

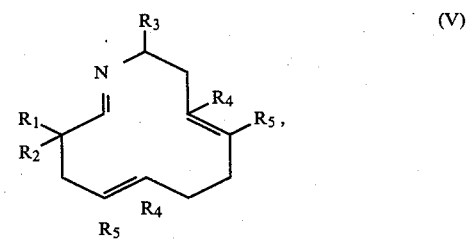

converting the compound of the formula V in an aqueous or aqueous-organic medium, in the presence of an inorganic acid not oxidising under the reaction conditions, such as hydrochloric acid or sulphuric acid, into a compound of the formula VI

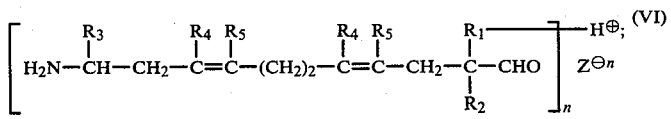

and catalytically hydrogenating the compound of the formula VI to yield a compound of the formula VII

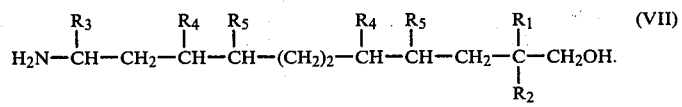

In the above formulae, $R_1$ to $R_3$ have the meanings given under the formula I, $R_4$ and $R_5$ independently of one another represent alkyl having 1–4 C atoms, but preferably each represent hydrogen, Z represents the anion of an inorganic acid not oxidising under the reaction conditions, and n represents an integer corresponding to the valency of Z.

Suitable catalysts for the reaction to the 1-aza-1,5,9-cyclododecatrienes of the formula V are described, for example, in the German Offenlegungsschrift No. 2,330,087. Preferred catalysts are those which are obtained in situ by reduction of a nickel compound free from carbon monoxide, such as nickel stearate and particularly nickel acetylacetonate, with halogen-free metal aryls or metal alkyls, for example ethoxydiethyl aluminium, in the presence of an aryl- or alkylphosphine, or in the presence of an aryl- or alkylphosphite. The hydrolysis to the compounds of the formula VI is performed advantageously in an aqueous medium in the presence of sulphuric acid. Platinum/charcoal catalysts or palladium/charcoal catalysts are advantageously used for the catalytical hydrogenation to give the amino alcohols of the formula VII.

Fungi occurring on plants or on parts of plants can be controlled or destroyed with the stated active substances. These are suitable for example for combating phytopathogenic fungi of the classes Basidiomycetes, such as rust fungi (e.g. Puccinia), *Fungi imperfecti* (e.g. Cercospora) and Phycomycetes (e.g. Oomycetes, such as Plasmopara and Phytophthora).

Amino alcohols of the formula VII can be used also as active substances for regulating plant growth.

EXAMPLE 1

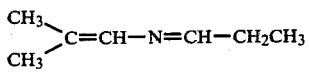

25 g (0.223 mol) of potassium tert-butylate is suspended in one liter of anhydrous diethyl ether. With continuous stirring, 921 g (8.3 mols) of isobutylidene-allylamine is then added dropwise, in the course of 1 hour, in such a way that the temperature of the reaction mixture does not exceed 20° C. After completion of the dropwise addition, stirring is continued at 20°–22° C. for a further 5 hours. The reaction is then discontinued and, at a bath temperature of 40° C. and a pressure of 200–250 Torr, the solvent is distilled over. The residue is distilled, at a bath temperature of 70° C./0.1 Torr, into a distillation receiver cooled with $CO_2$/methanol. Subsequent fine distillation yields 808 g (7.93 mols) of N-propylidene-(2-methylpropenylamine), corresponding to a yield of 87.6% of theory; b.p. 122° C.; $n_D^{20}=1.471$.

Analysis for $C_7H_{13}N$ (molecular weight 111): calculated: C: 75.62%; H: 11.79%; N: 12.60%, found: C: 75.3%; H: 11.9%; N: 12.2%.

MS spectrum: molecular peak 111, masses of the fragments 96, 82, 55.

$^1$H-NMR spectrum $\tau$ (ppm): 2.45(t), 3.65(s), 7.67(m), 8.03(s), 8.23(s), 8.87(t) in the ratio of 1:1:2:3:3:3.

IR spectrum (liquid): $\nu$ (C=C—N=C) —1665, 1635 cm$^{-1}$, $\delta$ (CH$_3$) —1375 cm$^{-1}$.

EXAMPLE 2

If the procedure is carried out as described in Example 1 except that 1 liter of toluene is used instead of 1 liter of diethyl ether, and the reaction temperature is raised to 40° C., propylidene-(2-methylpropenylamine) is obtained in a yield of 82% of theory.

EXAMPLE 3

If the procedure is carried out as described in Example 1 except that 1 liter of n-pentane is used instead of 1 liter of diethyl ether, there is obtained, after a reaction time of 20 hours at 30° C., propylidene-(2-methyl-propenylamine) in a yield of 70% of theory.

EXAMPLE 4

If the procedure is carried out as described in Example 1 except that 1 liter of tetrahydrofuran is used instead of 1 liter of diethyl ether, there is obtained, after a reaction time of 3.5 hours at 20° C., propylidene-(2-methylpropenylamine) in a yield of 81% of theory.

EXAMPLE 5

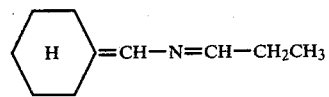

The procedure is carried out as described in Example 1, with the use however in this case of 5 g of potassium tert-butylate, 240 g (1.59 mols) of cyclohexyl-methylidene-allylamine and 250 ml of tetrahydrofuran. After a reaction time of 1 hour at 30° C., there is obtained 199 g (1.32 mols) of propylidene(cyclohexylidene-methylamine), corresponding to a yield of 83% of theory; b.p. 51°–53° C./0.3 Torr; $n_D^{20}=1.5072$.

Analysis for $C_{10}H_{17}N$ (molecular weight 151): calculated: C: 79.41%; H: 11.33%; N: 9.26%; found: C: 79.6%; H: 11.3%; N: 9.4%.

Mass spectrum: molecular peak 151, masses of the fragments 136, 122, 168, 95.

IR spectrum (liquid): $\nu$ (C=C—N=C) —1670, 1640 cm$^{-1}$, $\delta$ (CH$_3$) —1375 cm$^{-1}$.

$^1$NMR spectrum $\tau$ (ppm): 2.41(t), 3.67(s), 7.3–7.9(m), 8.4(s), 8.85(t) in the ratio of 1:1:6:6:3.

EXAMPLE 6

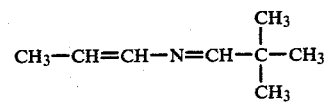

The procedure is carried out as described in Example 1, with the use however in this case of 10 g of potassium tert-butylate, 330 g (2.95 mols) of (2,2-dimethylpropylidene)allylamine and 450 ml of benzene. After a reaction time of 3.5 hours at 40° C., there is obtained 325 g (2.9 mols) of (2,2'-dimethyl-propylidene)-propenylamine, corresponding to a yield of 98.5% of theory, as a cis/trans isomeric mixture in the weight ratio of 65:35; b.p. 110° C.; $n_D^{20}=1.4487$.

Analysis for $C_8H_{15}N$ (molecular weight 125): calculated: C: 76.74%, H: 12.07%; N: 11.19%; found: C: 76.92%, H: 12.04%; N: 11.41%.

MS spectrum: molecular peak 125, masses of fragments 110, 82, 68.

$^1$H-NMR spectrum (cis isomer) $\tau$ (ppm): 2.55(s), 3.5(m), 4.7(quin), 8.1(dd), 8.95(s) in the ratio of 1:1:1:3:9.

$^1$H-NMR spectrum (trans isomer) $\tau$ (ppm): 2.55(s), 3.5(m), 4.1(sex), 8.25(dd), 8.95(s) in the ratio of 1:1:1:3:9.

EXAMPLE 7

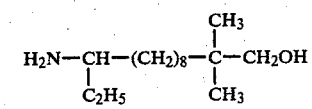

Under a protective gas (argon), 2.8 g (0.011 mol) of nickel acetylacetonate and 2.8 g (0.011 mol) of triphenylphosphine in 75.7 g of absolute toluene, in which 61.0 g (1.13 mols) of 1,3-butadiene is dissolved, are reduced with 3 g (0.023 mol) of ethoxydiethyl aluminium at 0° to 20° C. The reaction mixture is stirred for one hour at 20° C., and is then cooled to 0° C. To the solution at this temperature is then added all at once 48.5 g (0.437 mol) of N-propylidene-(2-methylpropenylamine) [1-ethyl- 4,4-dimethyl-2-aza-1,3-butadiene]. The reaction mixture is now heated to 40° C., and is kept at this temperature for 2 hours with continuous stirring. The reaction solution is then cooled to 0° C.; for the purpose of inactivating the catalyst, 17.2 g (55.5 mols) of triphenylphosphite is added, and the reaction mixture is repeatedly distilled. Distillation yields a total amount of 63.0 g (0.283 mol) of 3,3-dimethyl-12-ethyl-1-aza-1,5,9-cyclododecatriene; yield 64.9% of theory, relative to reacted N-propylidene-(2-methylpropenylamine) (conversion 100%); b.p. 65°–66° C./0.005 Torr; $n_D^{20} = 1.4864$.

199 g (0.91 mol) of 3,3-dimethyl-12-ethyl-1-aza-1,5,9-cyclododecatriene is added dropwise, in the course of 15 minutes, to a solution of 150 g (1.53 mols) of sulphuric acid in one liter of water. Impurities are removed by means of subsequent steam distillation for 20 minutes. The aqueous sulphuric acid solution is then hydrogenated under normal pressure at 20°–25° C. in the presence of a platinum/charcoal catalyst (5% by weight of platinum), with absorption of 3 mols of hydrogen, to yield 2,2-dimethyl-11-ethyl-11-aminoundecanol. After removal of the catalyst by filtration, the aqueous solution is neutralised with concentrated sodium hydroxide solution; the amino alcohol separating out is extracted with toluene, and distilled to thus obtain 149 g (0.613 mol) of 2,2-dimethyl-11-ethyl-11-aminoundecanol corresponding to a yield of 67.4% of theory; b.p. 118° C./0.05 Torr; $n_D^{20} = 1.4656$.

The above amino alcohol was tested with regard to its fungicidal action, especially with regard to its action against *Cercospora personata* (= *C. arachidicola*) on peanut plants: 3-week old peanut plants were sprayed with a spray liquor prepared from wettable powder of the active substance (0.02% by weight of active substance). After about 12 hours, the treated plants were dusted with a conidiospore suspension of the fungus. The infested plants were then incubated for about 24 hours at >90% relative humidity, and subsequently placed in a greenhouse at about 22° C. The fungus infestation was assessed after 12 days. Compared with untreated control plants, the plants which had been treated with the said active substance showed a slight fungus infestation.

EXAMPLE 8

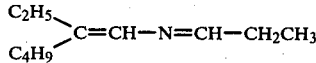

The procedure is carried out as described in Example 1 with the use however in this case of 10 g of potassium tert-butylate, 800 g (4.79 mols) of (2-ethylhexylidene)-allylamine and 600 ml of tetrahydrofuran. After a reaction time of 2 hours at 35° C., there is obtained 682 g (4.08 mols) of N-propylidene-(2-ethylhexen-1-yl-amine), corresponding to a yield of 85.2% of theory (isomeric mixture in the weight ratio of 55:45); b.p. 53°–56° C./1 Torr; $n_D^{20} = 1.4698$.

Analysis for $C_{11}H_{21}N$ (molecular weight 167): calculated: C: 78.97%; H: 12.65%; N: 8.37%; found: C: 78.65%; H: 12.73%; N: 8.29%.

MS spectrum: molecular peak 167; masses of the fragments 152, 138, 124, 96, 69, 55.

IR spectrum (liquid): $\nu$ (C=C—N=C) —1665, 1640 $cm^{-1}$; $\delta$ ($CH_3$) —1375 $cm^{-1}$.

$^1$H-NMR spectrum $\tau$ (ppm): 2.42(t), 3.65(d), 7.4–8.1(m), 8.6(m), 8.85(t) and 9.05(dt) in the ratio of 1:1:6:4:3:6.

I claim:

1. A compound of the formula I

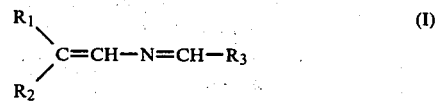

wherein
R₁ and R₂ independently of one another represent alkyl having 1–8 C atoms, or together with the bond C atom they represent a cycloaliphatic ring having 4–8 C atoms, and
R₃ represents ethyl; or
R₁ represents alkyl having 1–8 C atoms,
R₂ represents hydrogen, or alkyl having 1–8 C atoms, and
R₃ represents tertiary alkyl having 4–8 C atoms.

2. A compound of the formula I according to claim 1, wherein R₁ and R₂ independently of one another represent alkyl having 1–4 C atoms; or together with the bond C atom they represent cyclopentyl or cyclohexyl, and R₃ represents ethyl.

3. A compound of the formula I according to claim 1, wherein R₁ represents alkyl having 1–4 L C atoms, R₂ represents hydrogen, or alkyl having 1–4 C atoms, and R₃ represents tert-butyl.

4. A compound of the formula I according to claim 1, wherein R₁ and R₂ each represent methyl, and R₃ represents ethyl; or wherein R₁ represents methyl, R₂ represents hydrogen, and R₃ represents tert-butyl.

5. A compound as claimed in claim 1 having the formula

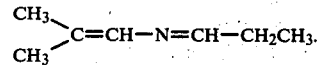

6. A compound as claimed in claim 1 having the formula

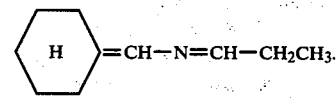

7. A compound as claimed in claim 1 having the formula

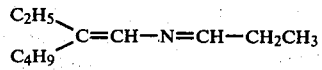

* * * * *